United States Patent
Marcum

(10) Patent No.: US 10,076,537 B2
(45) Date of Patent: Sep. 18, 2018

(54) GLYCOSAMINOGLYCAN COMPOSITION AND METHOD OF USE FOR KIDNEY STONE REMOVAL

(71) Applicant: ARTHRODYNAMIC TECHNOLOGIES, ANIMAL HEALTH DIVISION, INC., Lexington, KY (US)

(72) Inventor: Frank D. Marcum, Lexington, KY (US)

(73) Assignee: ARTHRODYNAMIC HOLDINGS, LLC, Lexington, KY (US)

( * ) Notice: Subject to any disclaimer, the term of this patent is extended or adjusted under 35 U.S.C. 154(b) by 12 days.

(21) Appl. No.: 15/307,465

(22) PCT Filed: May 4, 2015

(86) PCT No.: PCT/US2015/028984
§ 371 (c)(1),
(2) Date: Oct. 28, 2016

(87) PCT Pub. No.: WO2015/168671
PCT Pub. Date: Nov. 5, 2015

(65) Prior Publication Data
US 2017/0049803 A1    Feb. 23, 2017

Related U.S. Application Data

(60) Provisional application No. 61/987,542, filed on May 2, 2014.

(51) Int. Cl.
| | | |
|---|---|---|
| *A61K 31/728* | (2006.01) | |
| *A61K 31/737* | (2006.01) | |
| *A61K 31/7008* | (2006.01) | |
| *A61K 47/36* | (2006.01) | |
| *A61K 9/00* | (2006.01) | |

(52) U.S. Cl.
CPC .......... *A61K 31/737* (2013.01); *A61K 9/0019* (2013.01); *A61K 31/7008* (2013.01); *A61K 31/728* (2013.01); *A61K 47/36* (2013.01)

(58) Field of Classification Search
None
See application file for complete search history.

(56) References Cited

U.S. PATENT DOCUMENTS

| | | |
|---|---|---|
| 5,618,917 A | 4/1997 | Toback et al. |
| 6,979,679 B2 | 12/2005 | Marcum |
| 7,485,629 B2 | 2/2009 | Marcum |
| 7,504,387 B2 | 3/2009 | Marcum |
| 7,803,787 B2 | 9/2010 | Marcum et al. |
| 8,455,458 B2 | 6/2013 | Marcum et al. |
| 8,580,766 B2 | 11/2013 | Marcum |
| 8,871,742 B2 | 10/2014 | Marcum et al. |
| 9,186,375 B2 | 11/2015 | Marcum et al. |
| 9,381,211 B2 | 7/2016 | Marcum et al. |
| 2003/0114416 A1 | 6/2003 | Pulaski et al. |
| 2006/0067927 A1 | 3/2006 | Chandrasekaran et al. |
| 2006/0269512 A1 | 11/2006 | McDougal et al. |
| 2006/0292250 A1 | 12/2006 | Giampapa |
| 2008/0103481 A1 | 5/2008 | Vogel et al. |
| 2009/0137525 A1 | 5/2009 | Marcum |
| 2013/0180389 A1 | 7/2013 | Sullivan |
| 2015/0240211 A1 | 8/2015 | Coleman et al. |

OTHER PUBLICATIONS

Osborne, IC Daily Fact #22—Bladder Instillations & Catheters—IC Awareness Month, internet article, http://www.icawareness.org/ic-daily-fact-22-bladder-instillations-catheters, Sep. 23, 2012.*
PCT International Search Report and Written Opinion for PCT Application No. PCT/US2015/028984 dated Jul. 28, 2015 (6 pages).

* cited by examiner

*Primary Examiner* — Layla D Berry
(74) *Attorney, Agent, or Firm* — Eversheds Sutherland (US) LLP

(57) ABSTRACT

The invention provides compositions and methods of use thereof, in conjunction with the treatment and prevention of kidney and ureteral stones and related urinary tract conditions in man or in animals. Specifically provided are compositions formulated for direct instillation into the kidney, bladder, ureter, and urethra of the urinary tract before, during, and after the treatment of kidney and ureteral stones, such as with lithotripsy to alleviate or reduce at least one symptom associated therewith, and to facilitate the stones passing through the kidney, bladder, ureter, urethra and urinary tract. Compositions of the invention can comprise therapeutic amounts of: chondroitin sulfate and hyaluronan, and optionally include N-acetyl D-glucosamine.

20 Claims, No Drawings

GLYCOSAMINOGLYCAN COMPOSITION AND METHOD OF USE FOR KIDNEY STONE REMOVAL

CROSS REFERENCE TO RELATED APPLICATIONS

This application claims the priority benefit of PCT/US2015/028984 filed on May 4, 2015 which claims priority benefit to U.S. Provisional Patent Application No. 61/987,542 filed May 2, 2014, the entire contents of which are hereby incorporated by reference.

FIELD OF INVENTION

The invention is generally directed to the treatment and prevention of kidney and ureteral stones and at least one symptom associated therewith. Specifically, the invention relates to compositions comprising of glycosaminoglycans and glycosaminoglycan precursors specially formulated for use in conjunction with lithotripsy for the removal of kidney and ureteral stones and related urinary tract conditions, and for ureter stenting assistance.

BACKGROUND OF THE INVENTION

Stone disease is among the most painful and prevalent urological disorders. More than a million kidney stone cases are diagnosed each year with an estimated 10 percent of Americans destined to suffer from kidney stones at some point in their lives. The incidence of urolithiasis, or stone disease, is about 12% by age 70 for males and 5-6% for females in the United States. The debilitating effects of kidney stones are quite substantial, with patients incurring billions of dollars in treatment costs each year. Scientists do not always know what makes stones form. While certain foods may promote stones in susceptible people, researchers do not believe that eating specific items will cause stones in people who are not vulnerable. Yet factors such as a family or personal history of kidney stones and other urinary infections or diseases have a definite connection to this problem. Climate and water intake may also play a role in stone formation.

Normally, urine contains many dissolved substances. At times, some materials may become concentrated in the urine and form solid crystals. These crystals can lead to the development of stones when materials continue to build up around them. Stones formed in the kidney are called kidney stones. A ureteral stone is a kidney stone that has left the kidney and moved down into the ureter. The majority of stones contain calcium, with most of it being comprised of a material called calcium oxalate. Other types of stones include substances such as calcium phosphate, uric acid, cystine and struvite.

Stones form when there is an imbalance between certain chemical urinary components such as calcium, oxalate and phosphate. These chemical components either promote crystallization while others inhibit it. The most common stones contain calcium in combination with oxalate and phosphate. A less common type of stone is caused by infection in the urinary tract. This type of stone is called a struvite or infection stone. Much less common are the pure uric acid stones. Much rarer is the hereditary type of stones called cystine stones and even more rare are those linked to other hereditary disorders.

Although most stone formers do not have a medical condition that directly leads to their stone development, conditions do exist that place patients at high risk for stone formation. For example, stones can form because of obstruction to urinary passage like in prostate enlargement or stricture disease. Stone formation has also been linked to hyperarathyrodism, an endocrine disorder that results in more calcium in the urine. Susceptibility can also be raised among the people with rare hereditary disorders such as cystinuria (formation of cystine stones in the kidneys, ureter, and bladder or primary hyperoxaluria (excessive urinary excretion of oxalate).

Another condition that can cause stones to form is absorptive hypercalciuria, a surplus of calcium in the urine that occurs when the body absorbs too much from food. Another condition that results in a high level of calcium in the urine is resorptive hypercalciuria where the kidney leaks calcium into the urine. The high levels result in calcium oxalate or phosphate crystals forming in the kidneys or urinary tract. Similarly, hyperuricosuria, excess uric acid tied to gout or the excessive consumption of protein-rich products, may also trigger kidney stones. Consumption of calcium pills by a person who is at risk to form stones, certain diuretics or calcium-based antacids may increase the risk of forming stones by increasing the amount of calcium in the urine. Calcium oxalate stones may also form in people who have chronic inflammation of the bowel or who have had an intestinal bypass operation or ostomy. This is because of loss of more water from the body as well as absorption of oxalate from the intestine.

Once stones form in the urinary tract, they often grow with time and may change location within the kidney. Some stones may be washed out of the kidney by urine flow and end up trapped within the ureter or pass completely out of the urinary tract. Stones usually begin causing symptoms when they block the outflow of the urine from the kidney leading to the bladder because it causes the kidney to stretch. Usually, the symptoms are extreme pain which often begins suddenly as the stone moves in the urinary tract, causing irritation and blockage. Typically, a person feels a sharp, cramping pain in the back and in the side of the area of the kidney or in the lower abdomen, which may spread to the groin. Sometimes a person will complain of blood in the urine, nausea and vomiting. While stones may not produce any symptoms, they can be growing, causing irreversible damage to kidney function. More commonly, however, if a stone is not large enough to prompt major symptoms, it still can trigger a dull ache that is often confused with muscle or intestinal pain. If the stone is too large to pass easily, pain continues as the muscles in the wall of the tiny ureter try to squeeze the stone along into the bladder. One may feel the need to urinate more often or feel a burning sensation during urination. If the stone is close to the lower end of the ureter at the opening into the bladder, a person will frequently feel like they have not fully completed urination. If fever or chills accompany any of these symptoms, then there may be an infection.

Unfortunately, kidney stones are a recurrent disease. In general, the lifetime recurrence risk for a stone former is thought to approach 50%. Stone prevention, therefore, is essential, e.g., medication or diet should be changed to reduce recurrence risk.

Stone size, the number of stones and their location are perhaps the most important factors in deciding the appropriate treatment for a patient with kidney stones. The composition of a stone, if known, can also affect the choice of treatments. Options for surgical treatment of stones include Extracorporeal Shock Wave Lithotripsy (ESWL), Ureteroscopy (URS), Percutaneous nephrolithotomy (PNL), and Open Surgery. ESWL is the most frequently used procedure for eliminating kidney stones non-invasively by using sound waves. The technology is only effective if the kidney is functioning well and there is no blockage to the passage of stone fragments. Further, one ESWL session by itself may not free the ureter of all stone material, and either a repeat ESWL session or treatment with another approach may be necessary. ESWL is not the ideal treatment choice for all patients. Patients who are pregnant, obese, have obstruction past the stone, have abdominal aortic aneurysms, urinary tract infections or uncorrected bleeding disorders should not have ESWL. In addition, certain factors such as stone size, location and composition may require other alternatives for stone removal. Moreover, because of possible discomfort during the procedure, some anesthesia or some form of sedation is generally needed. While shock wave lithotripsy is considered safe and effective, it can still cause complications. Most patients have blood in their urine for a few days after treatment. Bruising and minor discomfort in the back or abdomen from the shock waves are also common. To reduce the risk of complications, urologists usually tell their patients to avoid aspirin and other drugs that affect blood clotting for several weeks before treatment. Another complication may occur if the shattered stone particles cause discomfort as they pass through the urinary tract. In some cases, the urologist will insert a small tube called a stent through the bladder into the ureter to help the fragments pass.

Therefore, there exists a need in the art for preventing or treating kidney and ureteral stones while reducing and alleviating symptoms and complications associated therewith.

SUMMARY OF THE INVENTION

An object of the invention is to provide a composition and method of use thereof, in conjunction with lithotripsy and other surgical procedures for the removal, treatment and prevention of kidney and ureteral stones and associated urinary tract conditions, by providing a glycosaminoglycan composition adapted for a direct instillation into kidney, ureter, bladder, and through a catheter or a stent into the urinary tract to prevent, alleviate or lessen, and treat at least one symptom associated with kidney and ureteral stones, and related urinary tract conditions in man or in animals.

In certain embodiments, the invention provides methods of preventing or treating kidney stones or ureter stones with a glycosaminoglycan composition adapted for use as a medical device that is suitable for direct intra-kidney, ureter, and bladder instillation, wherein the composition comprises therapeutic amounts of: chondroitin sulfate in combination with hyaluronan (hyaluronic acid), which may optionally be in solution and suspension with N-acetyl D-glucosamine. In other embodiments, the invention provides a composition adapted for administration through a catheter or stent to the ureter and urinary tract for coating the ureter and urinary tract, wherein the composition comprises therapeutic amounts of: chondroitin sulfate in combination with hyaluronan (hyaluronic acid), which may optionally be in solution and suspension with N-acetyl D-glucosamine.

In certain embodiments, for example, the therapeutic amount of chondroitin sulfate can be from about 0.1 to 10 grams of chondroitin sulfate and the therapeutic amount of hyaluronic acid can be from about 10 mg to 1.0 gram per unit dose of the composition. In certain embodiments, the composition comprises about 10-250 mg/ml chondroitin sulfate and about 1-25 mg/ml hyaluronic acid. The chondroitin sulfate may preferably comprise a mixture of CS4 and CS6 chondroitin sulfate wherein the mixture can be from about 70% CS4 to about 30% CS4 and from about 30% CS6 to about 70% CS6. In addition, in some embodiments of the invention, the hyaluronic acid (HA) may be a Streptococcus derived (synthetically produced) HA having a molecular weight of at least about 250,000 Daltons and optionally may be at least about 500,000 Daltons. In other embodiments of the invention, the molecular weight of the HA of the invention is at least about 750,000 Daltons and optionally may be at greater than about 1,000,000 Daltons.

The compositions of certain embodiments of the invention provide a chondroitin sulfate (as CS4 and CS6) adapted for direct kidney, ureter, and bladder instillation, or administering to the urinary tract through a catheter and coating the urinary tract, that is in an effective combination with hyaluronic acid. The chondroitin sulfate of the compositions provided herein can be in solution or suspension with hyaluronic acid.

In certain embodiments of the invention, the compositions may further optionally include N-acetyl D-glucosamine. In certain embodiments, the hyaluronic acid and chondroitin sulfate of the composition is in a solution or suspension with N-acetyl D-glucosamine The N-acetyl D-glucosamine provided in the compositions of the invention may provide a bridge to cross-link with HA at its binding site as well as acting as a solution carrying precursor of the HA/CS link molecule versican/aggregan for the purpose of providing a supramolecular complex with link proteins to form a strongly hydrated space filling gel of poly-anionic glycosaminoglycan chains covalently attached to the core and contributing to the strength of GAG layers of the kidney, ureter, bladder, as well as the urinary tract.

The invention provides that the composition comprising therapeutic amounts of chondroitin sulfate in combination with hyaluronic acid, and optionally in combination with N-acetyl D-glucosamine, in a solution and suspension, can be used to a subject in need before, during, and after the treatment, e.g., lithotripsy and other surgical procedures, and preventive methods known in the art for kidney and ureter stones, and other related urinary tract conditions. In certain embodiments, the composition of the invention alleviates and reduces pain and inflammation or infections associated with kidney and ureteral stones. In other embodiments, the composition of the invention facilitates stones passing through the kidney, ureter, bladder, and urinary tract in the urine. In other embodiments, the composition of the invention can be used to assist inserting and passing through a catheter and a stent by coating and lubricating the catheter and stent used in a surgical procedure for treating kidney and ureteral stones, and for ureter stent assistance.

Compositions suitable for use in the present invention are described, for example, in U.S. Pat. No. 7,485,629 and U.S. Pat. No. 8,580,766, which are incorporated herein by reference in their entireties.

DETAILED DESCRIPTION OF THE INVENTION

Additional objects, advantages and other novel features of the invention will be set forth in part in the description that follows and in part will become apparent to those skilled in the art upon examination of the foregoing or may be learned with the practice of the invention. Additionally, throughout this document, various publications and patents have been cited, the contents of which are incorporated herein by reference in their entirety.

Set forth in greater detail below are specific details related to compositions and methods of use thereof, in conjunction with the treatment, e.g., lithotripsy and other surgical procedures known in the art, and/or prevention of kidney, bladder, and/or ureteral stones and/or related urinary tract conditions. In particular, the present invention provides specific teachings related to a composition and related method of use thereof, in conjunction with the treatment, e.g., lithotripsy and other surgical procedures known in the art for removal, and/or prevention of kidney, bladder, and ureter stones, and related urinary tract conditions, by providing a composition adapted for direct kidney, ureter, or bladder instillation which can be used as a treatment or prevention to alleviate or lessen at least one symptom, such as pain, associated with kidney, bladder, and/or ureteral stones or related urinary tract conditions in man or in animals. The examples set forth herein are in no way intended to limit the scope of the invention. Those of skill in the art will realize that, given the teachings provided herein, many variations of the methods are possible that will fall within the scope of the invention.

In certain embodiments, the invention provides a composition adapted for direct parenteral instillation into the kidney, bladder, and ureter, such as through a catheter into the ureter and the urinary tract, by providing a coating is the urinary tract, that is useful to alleviate or lessen at least one symptom associated with kidney and ureteral stones or related urinary tract conditions, such composition comprises therapeutic amounts of: chondroitin sulfate and hyaluronan (hyaluronic acid), and may optionally include N-acetyl D-glucosamine. The invention further provides that the composition comprising therapeutic amounts of chondroitin sulfate in combination with hyaluronic acid, and optionally in combination with N-acetyl D-glucosamine, in a solution and suspension, can be used to a subject in need before, during, and after the treatment, e.g., lithotripsy and other surgical procedures, now known or later developed, and preventive methods now known or later developed in the art for kidney and ureteral stones, and associated relevant urinary tract conditions.

While not wishing to be bound to any particular theory, it is believed that the glycosaminoglycans (GAGs) present in the compositions and methods herein provide a benefit primarily through a mechanical mode of action to create a protective barrier to epithelium and endothelium tissues, and to lubricate stones and stone fragments to facilitate passage through the walls of the kidney, bladder, ureter, as well as the urinary tract, while also lessening pain of the subject in need. Further, it is believed that the compositions and methods contribute to the return of homeostasis of walls of the kidney, bladder, ureter, as well as the urinary tract, through the supramolecular complex of strongly hydrated space filling gel of poly-anionic GAG chains covalently attached to the core of the GAG layer in the kidney, bladder, ureter, and the urinary tract, and providing physical strength to these tissues. In addition to those effects, the incorporation of chondroitin sulfate into the compositions provided herein helps slow down the inflammatory process, by liganding to the CD44 and TSG-6 ligand receptor sites acting directly on the enzymes and inflammatory mediators that are released when inflammation is present.

The sodium hyaluronate (hyaluronan or hyaluronic acid) provided by the compositions can serve to cover the surface or transitional epithelial lining/wall of the kidney, bladder, ureter, and urinary tract, with a thin coating of the above supramolecule. Hyaluronan can also directly acts as an inhibitor of inflammatory mediators by its direct effect on CD44 receptor ligands which mediates the migration of lymphocytes during inflammation. When present in the compositions of the invention, the N-acetyl D-glucosamine acts to link the supramolecular complex in solution as well as acting as a precursor to form new chains by the existing GAG layer.

It is also believed that the compositions and methods contribute to the inhibition of stone formation and growth (see, e.g., Escobar et al., Role of Sulfated Macromolecules in Urinary Stone Formation, Proceedings of the $9^{th}$ International Symposium on Biomineralization, Editorial Universitaria, Santiago, Chile, 2007, pp. 343-358)

The compositions of the invention provide a mixture comprised of the naturally occurring glycosaminoglycans: chondroitin sulfates CS4 and CS6, and hyaluronan (hyaluronic acid). Glycosaminoglycans are polysaccharides which occur widely in the animal kingdom. Glycosaminoglycans that are present in the tissues of vertebrate animals have mainly a linear structure which is repetition of a disaccharide units composed of two monosaccharides. Five kinds of glycosaminoglycans are found in the tissues and fluids of vertebrates: chondroitin sulfates, keratin sulfates, dermatin sulfates, heparin sulfates; hyaluronic acid and heparin.

Chondroitin sulfates are one component of certain embodiments of the compositions of the invention. In general, chondroitin sulfates are widely found in the connective tissues of animals in two forms of repeating disaccharides of D-glucouronic acid and N-acetyl galactosamine: CS4 sulfate where N-acetyl galactosamine holds an ester sulfate in its CS4 position or CS6 sulfate where the ester sulfate is in the CS6 position. Both CS4 and CS6 chondroitin sulfate function in the articular matrix as a major constituent. Chondroitin sulfates contribute to keep the intracellular matrix's normal characteristics through the binding with HA to form the core of the supramolecular complex, as well as slowing down the inflammatory process acting directly on the enzymes inhibiting the compliment cascade and by exhibiting anti-prostoglandin activity.

In particular, chondroitin sulfate is a long hydrophilic chain of repeating sugars. This glycosaminoglycan binds to proteoglycan molecules aiding in the attachment of the supramolecular complex to the core protein as well as the GAG tissue layer in the kidney, bladder, ureter, and urinary tract. Chondroitin in its sulfate form includes galactosamine, a primary substrate of hylauronan and a disaccharide pathway for proteoglycan synthesis secondary to the hexosamine pathways utilized for glycosaminoglycan production. Chondroitin stimulates the production of proteoglycans, glycosaminoglycans, and collagen, which are the building blocks of a healthy GAG layer of the bladder, kidney, ureter, and urinary tract. Chondroitin sulfate also inhibits the secretion of degenerative enzymes by the liganding CS4 on the TSG-6 receptor responsible for inflammation. Chondroitin Sulfates are non-toxic and work synergistically with glucosamine to hydrate and repair the GAG layer of the kidney, bladder, ureter, and urinary tract walls. Chondroitin sulfate also works synergistically with hyaluronic acid to form the supramolecular matrix core to increase viscosity of the compositions of the invention and thereby increase the coating/protective properties of compositions as they bind to the GAG layer of the kidney, bladder, ureter, and urinary tract walls. (see e.g., Coleman et al., "Hyaluronan Synovial Joints: Molecular Seiving, Concentration Polarization & Secretion Regulation in vivo", Matrix Biology Institute 2004).

Another component of certain embodiments of the compositions of the invention is hyaluronic acid (HA) also known as sodium hyaluronate or hyaluronan, which is a natural constituent of connective tissues and synovial fluid composed of repeating disaccharide units each consisting of D-glucoronic acid and N-acetyl D-glucosamine. Hyaluronan aids in providing nourishment and waste removal from the intracellular matrix. When combined with chondroitin sulfate, the exogenous hyaluronin present in the compositions of the invention acts synergistically with the chondroitin sulfate to aid in the treatment and prevention of at least one symptom associated with kidney and ureteral stones, and related urinary tract conditions.

Therefore, one embodiment of the invention provides a composition adapted for direct intra kidney, ureter, urethral and bladder parenteral installation, such as through a catheter, syringe or during open surgery, coating the urinary tract that is useful in conjunction with the removal treatment and prevention of kidney and ureteral stones, by providing a therapeutic amount of composition to alleviate or lessen at least one symptom associated with kidney and ureteral stones or a related urinary tract condition in man or in animals, the composition comprising or consisting essentially of therapeutic amounts of: chondroitin sulfate and hyaluronan, and optionally N-acetyl D-glucosamine, optionally in the substantial absence of other naturally occurring or synthetic glycosaminoglycans.

In general, the compositions of certain embodiments of the invention may optionally include N-acetyl D-glucosamine. N-acetyl D-glucosamine also possesses the ability to provide a bridge to cross-link with HA at its binding site as well as acting as a solution for carrying precursors of the HA/CS link molecule versican/aggregan for the purpose of providing a supramolecular complex with linking proteins to form a strongly hydrated space filling gel of poly-anionic glycosaminoglycan chains covalently attached to the core and contributing to the strength of the GAG layer in the kidney, ureter, and urinary tract.

N-acetyl D-glucosamine is also a derivative of glucose obtained by chemical hydrolysis of chitin. This polysaccharide is readily soluble in water and extremely bioavailable. N-acetyl D-glucosamine binds to glucuronic acid as well as galactose making it a precursor to hyaluronic acid, keratansulfate and chondroitin sulfate. This unique derivative aids a proteoglycan, collagen and glycosaminoglycan production. N-acetyl D-glucosamine has also been shown to aid in the healing of soft tissue injury.

The embodiments of the invention are safe and non-toxic in the therapeutic amounts as set forth herein. Each embodiment provides benefits in relation to the treatment and prevention to thereby alleviate, lessen or prevent at least one symptom associated with kidney and ureteral stones or a related urinary tract condition in man or in animals. Thus, it can be realized that certain of the compositions of this invention, e.g., those comprised of chondroitin sulfate, N-acetyl D-glucosamine and hyaluronic acid provide a combination for direct instillation into the kidney, ureter, bladder, as well as the urinary tract such as through a catheter, and for systemic use with desired mechanical properties, and metabolic precursors which advantageously stimulate the production of glycosaminoglycans including hyaluronic acid, proteoglycans and collagen, thereby assisting the body's natural repair mechanisms and as a coating for the kidney, ureter, bladder, and urinary tract epithelium and to inhibit certain inflammatory mediators by its direct effect on CD44 and TSG-6, and Lyve receptor sites.

Another important aspect of the compositions and methods of the invention is that they are adapted for direct instillation into the kidney, bladder, and ureter, and urinary tract and are especially well suited for use as a medical device for physical coating for tissue protection and lubrication, to assist in lavage or flushing of stones and fragments from the kidney, bladder, ureter, and the urinary tract, as well as to provide a regenerative coating to the epithelium. The highly negative ionic charge and unique characteristics of the compositions set forth herein act to directly trap or bind positively charged particles present in the kidney, bladder, ureter, and the urinary tract, e.g., free radicals released from the inflammatory processes, and physically remove such particles from the epithelial surface of the kidney, bladder, ureter, and urinary tract. Because of their capacity for multidimensional disposition, hydrophilic nature, prominent presence of negative charges and lubricating/coating capabilities, the compositions provided herein also exhibit selective permeability, and support for the damaged epithelium of the kidney, bladder, ureter, and the urinary tract of patient suffering from kidney and ureteral stones, which are essential characteristics to aid the return of the kidney and ureteral wall (epithelium and interstitial matrix etc.) to homeostasis.

Thus, in one embodiment, the compositions of the invention have been specially adapted for intra kidney, bladder, and ureter instillation and administration into the urinary tract through a catheter or coating the urinary tract, are sterile solutions or suspensions comprised of therapeutic amounts of chondroitin sulfate and hyaluronan (hyaluronic acid). In addition to the afore-mentioned agents, it can be appreciated by one of skill in the art that the compositions of the invention which are adapted for intra-kidney, bladder, and ureter instillation and administering into the urinary tract through a catheter or stent for assisting in insertion and providing coating of the urinary tract can also comprise preservatives, pharmaceutically active carriers, excipients, stabilizers, buffers, antimicrobial growth inhibitors and the like and the use of such is contemplated by the invention.

It is contemplated by the invention that the compositions provided herein may be useful in methods for the direct intra-kidney, bladder, and ureter instillation, and administering into the urinary tract through a catheter or stent for assisting inserting and providing coating and lubricating the urinary tract in conjunction with the treatment and prevention of kidney and ureteral stones. In certain embodiments the compositions of the invention are comprised of therapeutic amounts of chondroitin sulfate and hyaluronan (hyaluronic acid). In some embodiments, the compositions of the invention are sterile solutions and are suspensions comprised of chondroitin sulfate and hyaluronan. In other embodiments, the chondroitin sulfate and hyaluronic acid of the composition is in a solution of N-acetyl D-glucosamine.

It is contemplated that other formulations are possible and are within the scope of the invention, e.g., a powdered formulation suitable for reconstitution with a suitable injectable liquid or for addition to a preselected liquid suitable for instillation into the kidney, bladder, and ureter, as well as the urinary tract, e.g., lactated ringers or normal saline solution. In particular, it can be appreciated by one of skill in the art that the active agents of the compositions can be stored in a freeze dried or lyophilized state for reconstitution and use at a desired time.

In certain embodiments, the invention comprises a composition adapted for direct intra-kidney, bladder, and ureter instillation and administration into the urinary tract through a syringe, catheter or stent by assisting inserting and providing coating and lubricating the urinary tract comprised of chondroitin sulfate and hyaluronan, wherein the therapeutic amount of chondroitin sulfate is from between about 0.1 to 10 grams of a suitable chondroitin sulfate per unit dose of the composition. In certain embodiments, the therapeutic amount of chondroitin sulfate is about 10 mg/ml, 20 mg/ml, 30 mg/ml, 50 mg/ml, 100 mg/ml, 150 mg/ml, 200 mg/ml, and 250 mg/ml of the composition.

In one embodiment, the therapeutic amount comprises about 1 gram of CS4 chondroitin sulfate, or about 1 gram of CS6 chondroitin sulfate or about 1 gram of a mixture of CS4 and CS6 chondroitin sulfate per unit dose. In some embodiments, the therapeutic amount of chondroitin sulfate is about 1 gram of chondroitin sulfate comprised of about 40% CS4 chondroitin sulfate and about 60% CS6 chondroitin sulfate. In other embodiments, the chondroitin sulfate may comprise a mixture of CS4 and CS6 chondroitin sulfate wherein the mixture can be from about 70% CS4 to about 30% CS4 and from about 30% CS6 to about 70% CS6.

In certain embodiments, the therapeutic amounts of hyaluronan include from about 10 mg to about 1.0 g of hyaluronan per unit dose of the composition. In some embodiments, the therapeutic amount of hyaluronan is about 1 mg/ml, 2 mg/ml, 5 mg/ml, 10 mg/ml, 15 mg/ml, and 20 mg/ml of the composition.

It can be appreciated by one of skill in the art that the hyaluronan can be selected from among any of a number of commercially available sources such as sodium hyaluronate. Likewise there are numerous commercially available sources of chondroitin sulfate and N-acetyl D-glucosamine that are available for use in the compositions set forth herein. An exemplary commercially available composition contains purified hyaluronic acid (5 mg/ml), chondroitin sulfates C4 & C6 (100 mg/ml) in a 10% solution of N-acetyl-D-glucosamine 100 mg/ml).

In certain embodiments of the invention the compositions may optionally include therapeutic amounts of N-acetyl D-glucosamine that are from about 0.5 grams to about 1.5 grams per unit dose of the composition. In some embodiments, the therapeutic amount of N-acetyl D-glucosamine is about 1 gram per unit dose of the composition. In one embodiment, the CS and HA comprising the compositions of the invention are in about a 10% solution of N-acetyl D-glucosamine.

Another present embodiment of the invention provides a composition adapted for direct intra-kidney, bladder, and ureter instillation and administration into the urinary tract through a catheter or a stent for assisting an insertion of the catheter or stent and for direct coating of the urinary tract comprised of a sterile solution or suspension comprised of about 1 gram of chondroitin sulfate per 50 ml of composition (i.e., about 2% w/v or 200 mg/ml) as a mixture of about 40% CS4 and 60% CS6 chondroitin sulfate; and about 800 mg of hyaluronan (e.g., Na Hyaluronate) per 50 ml of the composition (i.e., about 1.6% w/v or 16 mg/ml). Still another embodiment of the invention provides compositions for direct intra-kidney and ureter instillation and administration into the urinary tract through a catheter or stent for assisting an insertion of the catheter or stent and for direct coating of the urinary tract comprised of a 5 cc/unit dose wherein the composition comprises about 500 mg of a suitable chondroitin sulfate and about 25 mg of a suitable hyaluronic acid (e.g. about 500,000 Daltons) in a 10% solution of N-acetyl D-glucosamine. Yet another embodiment of the invention provides compositions for direct intra-kidney, bladder, and ureter instillation and administration into the urinary tract through a catheter or stent for assisting an insertion of the catheter or stent and for direct coating of the urinary tract comprised of a 10 cc/unit dose wherein the composition comprises about 1000 mg of a suitable chondroitin sulfate and about 50 mg of a suitable hyaluronic acid (e.g. about 500,000 Daltons) in a 10% solution of N-acetyl D-glucosamine Making final compositions comprising desired final concentrations of chondroitin sulfate and sodium hyaluronate in the composition is routine and well known in the art.

One example of the embodiment of the invention comprises a method of using a 10 ml-50 ml unit dose of the composition. It can be appreciated that this unit dosage can be added to a suitable amount of a liquid selected for direct kidney, bladder, and ureter instillation, e.g., including but not limited to water, lactated ringers, normal saline, and DMSO. It can also be appreciated that the methods of the invention in conjunction with the treatment and prevention of kidney and ureteral stones, e.g., lithotripsy and other surgical procedures now known or later developed, can utilize more than one unit dose per treatment and the treatment regimen can vary depending upon the severity of the condition, age and health of the patient and the like.

One present embodiment of the invention provides a composition adapted for direct intra-kidney, bladder, and ureter instillation and administration into the urinary tract through a catheter or stent for assisting an insertion of the catheter or stent and for direct coating of the urinary tract which consists essentially of therapeutic amounts of chondroitin sulfate and hyaluronan.

In other embodiments the invention provides a composition adapted direct intra-kidney, bladder, and ureter instillation, and administration into the urinary tract through a catheter or direct coating the urinary tract which comprises therapeutic amounts of chondroitin sulfate; and hyaluronan wherein the molecular weight per unit dose of the composition is from between about 450,000 Daltons to about 1,100,000 Daltons. In some embodiments the invention provides a composition adapted for direct intra-kidney, bladder, and ureter instillation, and administration into the urinary tract through a catheter or direct coating the urinary tract which comprises therapeutic amounts of chondroitin sulfate; and hyaluronan wherein the molecular weight per unit dose of the composition is from between about 500,000 Daltons to about 1,000,000 Daltons. In other embodiments the invention provides a composition adapted direct intra-kidney, bladder, and ureter instillation and administration into the urinary tract through a catheter or direct coating the urinary tract which comprises therapeutic amounts of chondroitin sulfate and hyaluronan wherein the molecular weight per unit dose of the composition is from between about 550,000 Daltons to about 700,000 Daltons but is especially about 600,000 Daltons.

In yet other embodiments the invention provides a composition adapted direct intra-kidney, bladder, and ureter instillation and administration into the urinary tract through a catheter or stent for assisting the insertion of the catheter or stent and for direct coating and lubricating the urinary tract which comprises therapeutic amounts of chondroitin sulfate and hyaluronan wherein the molecular weight per unit dose of the composition is greater than about 450,000 Daltons. In some embodiments, the invention provides a composition adapted for direct intra-kidney, bladder, and ureter instillation and administration into the urinary tract through a catheter or stent for assisting the insertion of the catheter or stent and for direct coating and lubricating the urinary tract which comprises therapeutic amounts of chondroitin sulfate and hyaluronan wherein the molecular weight per unit dose of the composition is greater than about 550,000 Daltons.

In certain embodiments of the invention the compositions set forth herein can further comprise a therapeutic amount of a suitable antibiotic. Suitable antibiotics for use in the compositions provided herein include, but are not limited to any of the antibiotics that are known in the art for the treatment and prevention of infections and inflammations associated with kidney and ureteral stones and at least one symptom associated therewith. As can be appreciated by one of skill in the art, the choice of antibiotic and therapeutic amount can depend upon many factors including, but not limited to, e.g., the etiology of the infectious organism being treated or personal preference of the treating veterinarian or physician.

The compositions of the invention can also further comprise other therapeutic agents insofar as it is generally used as a therapeutic for kidney and ureteral stones. Examples of other such therapeutic agents include, but are not limited to, synthetic and non-synthetic corticosteroid agents, nonsteroidal anti-inflammatory drugs, antirheumatics, immunoregulators, immunosuppressors, and interleukin production inhibitors. Specific examples of corticosteroid agents include, but are not limited to dexamethasone, hydrocortisone, triamcinolone, betamethasone, predonisolone, methylpredonisolone, halopredone, beclomethasone and the like.

Specific examples of non-steroidal anti-inflammatory agents include, but are not limited to diclofenac, indomethacin, ibuprofen, ketoprofen, aspirin, diflunisal, fulfenamic acid, floctafenine, tolfenamic acid, sulindac, fenbufen, salicylic acid, acemetacin, proglumetacin, nabumetone, protizinic acid, thiaprofen, oxaprozin, loxoprofen, alminoprofen, zaltoprofen, flurbiprofen, flurbiprofen and the like.

In certain embodiments, the compositions of the invention can further comprise of at least one pyrazolyl benzenesulfonamide compound, e.g., as set forth in U.S. Pat. No. 5,756,529 and U.S. Pat. No. 5,466,823, the contents of which are incorporated herein by reference. In particular, the compositions of the invention can further comprise a diaryl substituted pyrazole useful for treatment of inflammation and pain. It is specifically contemplated that the compositions of the invention can further comprise therapeutic amounts of any of the class of diaryl substituted pyrazoles their isomers, analogs and metabolites. In particular, these compounds reduce inflammation and pain primarily via inhibition of cyclooxygenase-2 (COX-2). In a preferred embodiment of the invention, the compositions provided further comprise a non-steroidal agent that reduces inflammation and pain primarily via inhibition of cyclooxygenase-2 (COX-2) and with the substantial absence of inhibition of cyclooxygenase-1 (COX-1). Examples of suitable diaryl substituted pyrazoles for use in the compositions of the invention include, but are not limited to, celecoxib, rofecoxib and the like.

Examples of other agents which may be added to the core compositions set forth herein include, axetil, piroxicam, tenoxicam, ampiroxicam, meloxicam, D-penicillamine, bucillamine, gold sodium thiomalate, auranofin, lobenzarit, salazosulfapyridine, methotrexate, cyclophosphamide, azathioprine, mizoribine, cyclosporin and the like.

In certain embodiments, the invention also provides a composition adapted for direct intra-kidney, bladder, and ureter instillation comprised of therapeutic amounts of chondroitin sulfate; hyaluronan and a suitable antioxidant or free radical scavenger. In some embodiments, the compositions of the invention can further comprise a therapeutic amount of suitable superoxide dismutase (SOD) or other antioxidant including, but not limited to, examples set forth in U.S. Pat. No. 6,127,356 to Crapo et al., the contents of which are incorporated herein by reference.

In other embodiments, the invention provides a composition adapted for administration into the urinary tract through a catheter or stent for assisting the insertion of the catheter or stent and for direct coating and lubricating the urinary tract that is used in a method for the treatment and prevention of kidney and ureteral stones, such as lithotripsy and other surgical procedures; and to prevent, reduce, and treat at least one symptom associated with kidney and ureteral stones, such as pain and inflammation or infections; and to facilitate passing and eliminating the stones or stone fragments through the kidney, bladder, ureter, and urinary tract in humans in need. Such composition comprises therapeutic amounts of: chondroitin sulfate and hyaluronan. In other embodiments, the related inventive methods are provided to humans or animals in need.

The foregoing descriptions of certain embodiments of the invention have been presented for purposes of illustration and description. They are not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A method of treating a symptom associated with a kidney stone or a ureteral stone in a subject in need, comprising administering to the subject in need an effective amount of a composition comprising an effective amount of chondroitin sulfate and hyaluronan.

2. The method of claim 1, wherein said chondroitin sulfate is CS4, chondroitin sulfate, CS6 chondroitin sulfate, or a mixture of CS4 and CS6 chondroitin sulfate.

3. The method of claim 1, wherein said effective amount of chondroitin sulfate is between about 0.1 grams to about 10 grams per unit dose of the composition.

4. The method of claim 1, wherein said effective amount of hyaluronan is about 10 mg to about 1000 mg of hyaluronan per unit dose of the composition.

5. The method of claim 1, wherein said composition further comprises an effective amount of N-acetyl D-glucosamine.

6. The method of claim 5, wherein said effective amount of N-acetyl D-glucosamine is between about 0.5 grams to about 10 grams per unit dose of the composition.

7. The method of claim 1, wherein said composition further comprises an excipient to facilitate the treatment.

8. The method of claim 1, wherein said composition is a sterile solution or a sterile suspension.

9. The method of claim 1, wherein said composition is directly instilled into the kidney, bladder, or ureter, or urethra of the urinary tract of the subject in need.

10. The method of claim 9, wherein said composition is instilled before, during, or after a separate treatment for the kidney or ureteral stones.

11. The method of claim 10, wherein said treatment for the kidney or ureteral stones is lithotripsy or other surgical procedures.

12. The method of claim 1, wherein said composition is administered to the urinary tract of the subject in need through a catheter to coat the urinary tract of the subject in need.

13. The method of claim 1, wherein said symptom is urinary tract pain, inflammation, or infection.

14. The method of claim 1, wherein said composition facilitates kidney or ureteral stones or fragments thereof passing through the kidney, bladder, ureter, or urethra of the urinary tract of said subject.

15. A method to alleviate or reduce pain, inflammation, or infection associated with a kidney stone or a ureteral stone in man or in animals, comprising administering to a subject in need an effective amount of a composition comprising an effective amount of chondroitin sulfate and hyaluronan, before, during, or after a separate treatment of the kidney or ureteral stones.

16. The method of claim 15, wherein said treatment of kidney or ureteral stones is by lithotripsy or other surgical procedures.

17. The method of claim 15, wherein said composition further comprises an effective amount of N-acetyl D-glucosamine.

18. The method of claim 17, wherein said composition further comprises one or more excipients to facilitate the treatment.

19. The method of claim 15, wherein said composition further facilitates kidney or ureteral stones passing through the kidney, bladder, ureter, or urinary tract of said subject.

20. The method of claim 15, wherein said composition is directly instilled into the kidney, bladder, ureter, or urethra administered through a catheter.

* * * * *